(12) United States Patent
Sarig et al.

(10) Patent No.: US 6,444,382 B1
(45) Date of Patent: Sep. 3, 2002

(54) STRAIGHT LINE DEFECT DETECTION TOOL

(75) Inventors: Nimrod Sarig, Rosh Ha'Avin; Gadi Greenberg, Tel Aviv, both of (IL)

(73) Assignee: Applied Materials, Santa Clara, CA (US)

( * ) Notice: Subject to any disclaimer, the term of this patent is extended or adjusted under 35 U.S.C. 154(b) by 0 days.

(21) Appl. No.: 09/985,281

(22) Filed: Nov. 2, 2001

Related U.S. Application Data

(62) Division of application No. 09/497,391, filed on Feb. 3, 2000.

(51) Int. Cl.$^7$ .............................. G03F 9/00; G06K 9/00
(52) U.S. Cl. ......................... 430/30; 382/144; 382/149
(58) Field of Search ........................... 430/30; 382/144, 382/149

(56) References Cited

U.S. PATENT DOCUMENTS 5,699,447 A    12/1997    Alumot et al.

*Primary Examiner*—Christopher G. Young
(74) *Attorney, Agent, or Firm*—McDermott, Will & Emery LLP (57) ABSTRACT

A method and apparatus for inspecting the straightness of edges of features on a reticle is provided wherein the feature edges are analyzed for local defects as small groups of pixels, rather than pixel-by-pixel. In one embodiment, the reticle is imaged to produce pixels having a gray level and associated with an x and a y coordinate. A small array of pixels, such as a 2×2 array, that lays on an edge of the target feature is identified, a plane is calculated based on the x coordinate, the y coordinate and the gray level of each of the pixels in the array, and an angle α between a reference line and a line at the intersection of the calculated plane and a reference plane is calculated. Several other edge-straddling arrays adjacent to the first array are identified, their respective angles α are calculated, and all the α's are compared. If the α's are substantially equal, it is determined that the target feature edge is straight, and if the α's are not substantially equal, it is determined that the target feature edge is curved. A corresponding reference feature image is analyzed in the same way as the target feature image, and a defect is determined to exist in the target feature when the target feature edge is curved and the reference feature edge is straight.

10 Claims, 10 Drawing Sheets

STRAIGHT LINE DEFECT DETECTION TOOL

This application is a Divisional of Application Ser. No. 09/497,391 filed Feb. 3, 2000.

FIELD OF THE INVENTION

The present invention relates to a method for inspecting photolithographic reticles used in the manufacture of semiconductor devices, and more particularly for inspecting the edges of reticle features. The invention has particular applicability for in-line inspection of reticles with submicron design features.

BACKGROUND ART

Current demands for high density and performance associated with ultra large scale integration require submicron features, increased transistor and circuit speeds and improved reliability. Such demands require formation of device features with high precision and uniformity, which in turn necessitates careful process monitoring.

One important process requiring careful inspection is photolithography, wherein masks, or "reticles", are used to transfer circuitry features to semiconductor wafers. Typically, a series of such reticles are employed in a preset sequence. Each photolithographic reticle includes an intricate set of geometric features corresponding to the circuit components to be integrated onto the wafer, such as chrome features on a glass substrate. Each reticle in the series is used to transfer its corresponding features onto a photosensitive layer (i.e., a photoresist layer) which has been previously coated on a layer, such as a polysilicon or metal layer, formed on the silicon wafer. The transfer of the reticle features onto the photoresist layer is conventionally performed by an optical exposure tool such as a scanner or a stepper, which directs light or other radiation through the reticle to expose the photoresist. The photoresist is thereafter developed to form a photoresist mask, and the underlying polysilicon or metal layer is selectively etched in accordance with the mask to form features such as lines or gates on the wafer.

Fabrication of the reticle follows a set of predetermined design rules set by processing and design limitations. These design rules define, e.g., the space tolerance between devices and interconnecting lines and the width of the lines themselves, to ensure that the devices or lines do not overlap or interact with one another in undesirable ways. The design rule limitation is referred to as the "critical dimension" (CD), defined as the smallest width of a line or the smallest space between two lines permitted in the fabrication of the device. The design rule for most ultra large scale integration applications is on the order of a fraction of a micron.

Figure 1A:
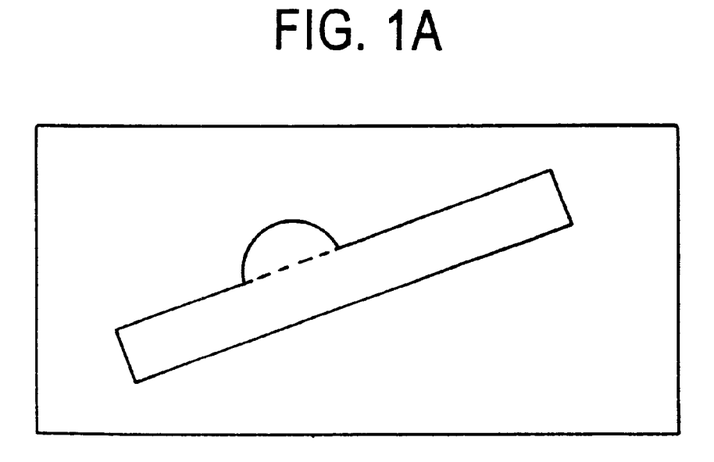
FIGS. 1A–1B illustrate possible defects of a feature on a reticle.
Figure 1B:
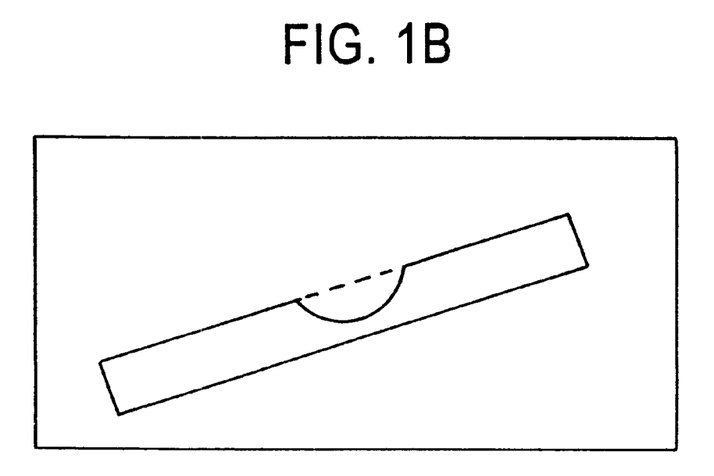

As design rules shrink and process windows (i.e., the margins for error in processing) become smaller, inspection and measurement of reticle features is becoming increasingly important, since even small deviations of feature sizes from design dimensions may adversely affect the performance of the finished semiconductor device. For example, features on the surface of the reticle include straight lines that extend across the surface of the reticle for forming interconnection lines or gates. FIGS. 1A–1B illustrate some typical defects of straight-line features. FIG. 1A shows an oversized portion of a line manifested as a "bump" on the line. The size of a non-defective feature is represented by the dotted line. FIG. 1B shows an undersized portion of a line manifested as a "bite" taken out of the line, and the size of a non-defective feature is represented by the dotted line.

Those skilled in the art recognize that a defect on the reticle, such as extra or missing chrome in straight lines as shown in FIGS. 1A–1B, may transfer onto the wafers during processing in a repeated manner, and therefore may significantly reduce the yield of the fabrication line. Therefore, it is of utmost importance to inspect the reticles and detect any defects thereupon. The inspection is generally performed by an optical system, such as the RT 8200 or ARIS-i reticle inspection system available from Applied Materials of Santa Clara, Calif. In the mask shop, i.e., where the masks and reticles are produced, the inspection system is used to scan the mask and compare the obtained image to the database used to create the mask. Differences between the image and the database are flagged as a suspect location.

More particularly, in typical prior art inspection schemes, the surface of the reticle is imaged, e.g., with a photomultiplier tube (PMT) or with a charge-coupled device (CCD) and the resulting image is an array of data elements called "pixels", each pixel being assigned a "gray level" corresponding to its intensity. In other words, each pixel is assigned a gray level proportional to the light transmitted, reflected, or both, depending on the system's design, by a portion of the reticle. For example, depending on the lighting and imaging technique used during scanning, a pixel located in the middle of an opaque feature will have a very high gray level, while a pixel in the space between features will have a low gray level, or vice versa. The pixels are typically analyzed one at a time and compared to pixels at the same respective location in a reference, such as a database, or the same location in a corresponding neighboring die, to determine the existence of defects. The gray levels of each of the pixels of the inspected reticle are also compared to the gray levels of their neighboring pixels to detect the edges of features for dimensional measuring purposes.

Disadvantageously, conventional reticle inspection tools cannot always accurately or reliably detect small or "local" defects in straight-line features. Prior art inspection tools lack the necessary sensitivity because they are limited to performing their analysis one pixel at a time. There is a need for a simple, fast, cost-effective methodology for inspection of reticles that enables accurate detection of straight line defects.

SUMMARY OF THE INVENTION

An advantage of the present invention is the ability to reliably detect defects in straight line features without increasing inspection time.

According to the present invention, the foregoing and other advantages are achieved in part by a method of inspecting a target feature formed on a surface, the method comprising imaging the target feature to produce a matrix of pixels representative of the target feature, each pixel having a gray level and associated with an x and a y coordinate corresponding to its respective location on the surface. A small array of pixels, such as a 2×2 array, that lays on an edge of the target feature is identified, a plane is calculated based on the x coordinate, the y coordinate and the gray level of each of the pixels in the array, and an angle α between a reference line (such as the positive x coordinate axis) and a line at the intersection of the calculated plane and a reference plane is calculated. Several other arrays adjacent to the first array and laying on the target feature edge are identified; e.g., about four other 2×2 arrays, and their respective angles α are calculated. The angles α are then compared. If the α's are substantially equal, it is determined that the target feature edge is straight. On the other hand, if the α's are not substantially equal, it is determined that the target feature edge is curved. A corresponding reference feature image is analyzed in the same way as the target feature image, and a defect is determined to exist in the target feature when the target feature edge is curved and the reference feature edge is straight, indicating an unwanted bite or a bump on the target feature edge.

Another aspect of the present invention is an inspection tool for carrying out the steps of the above method.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the present invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Conventional methodologies for inspecting features formed on the surface of a photolithographic reticle are not capable of accurately, reliably and economically detecting local defects in straight line features, such as bites or bumps. The present invention addresses and solves these problems by translating gray level data to local feature edge information, and mapping the edge information to a plurality of angular values, which can easily be compared to each other to determine whether an inspected feature edge is locally straight or locally curved, indicating the possibility of a bite or a bump on the edge. Such information can then be compared to corresponding information gleaned from a reference database to detect defects in the inspected feature. Because the present invention utilizes information gathered during the image-forming process (i.e. gray level information), it does not significantly increase inspection time, and can be employed in addition to conventional inspection techniques to increase the overall sensitivity of the inspection process.

According to the methodology of an embodiment of the present invention, a reticle is inspected using a conventional inspection tool, such as the RT 8200 or ARIS-i, which images a reticle (as with a scanning CCD array) as a matrix of pixels, each having a gray level and associated with an x and a y coordinate corresponding to its respective location on the reticle. A small array of pixels, such as a 2×2 array, that lays on an edge of the target feature is identified, as by determining that a significant contrast exists between the gray levels of the pixels in the array. For example, the differences of the gray levels of pairs of pixels in the array are calculated, and the differences are compared to a threshold value. Next, a plane is "fit" through the pixels; e.g., the four pixels in the edge-straddling array, as by a least squares method, using the x coordinate, the y coordinate and the gray level of each of the pixels in the array. An angle α between a reference line (such as the positive x coordinate axis) and the line at the intersection of the fitted plane and a reference plane, such as a plane through the x and y coordinates of the pixels, is then calculated.

Several other arrays adjacent to the first array and laying on the target feature edge are identified; e.g., about four other 2×2 arrays, and their respective angles α are calculated. The angles α are then compared. If the α's are substantially equal, it is determined that the target feature edge is straight in the proximity of the analyzed pixel groups. On the other hand, if the α's are not substantially equal, it is determined that the target feature edge is curved in the proximity of the analyzed pixel groups. The above-described analysis is also carried out on a corresponding reference feature image obtained from a reference database. A defect is determined to exist in the target feature when the target feature edge is curved and the reference feature edge is straight.

Thus, in the present methodology, the gray level information of small groups of pixels is analyzed to detect a feature edge and identify groups of pixels straddling an edge. Then, the gray level and coordinate information of the pixel groups is mapped to angular values, which are compared to each other to determine if the feature edge is locally straight or curved. Since the present invention analyzes small numbers of pixels at a time (e.g., four pixels at a time), it is able to detect local curvature of extremely small reticle features. The present invention's sensitivity enables early detection of straight-line defects that would not be readily or reliably detected by prior art inspection techniques.

Figure 2:
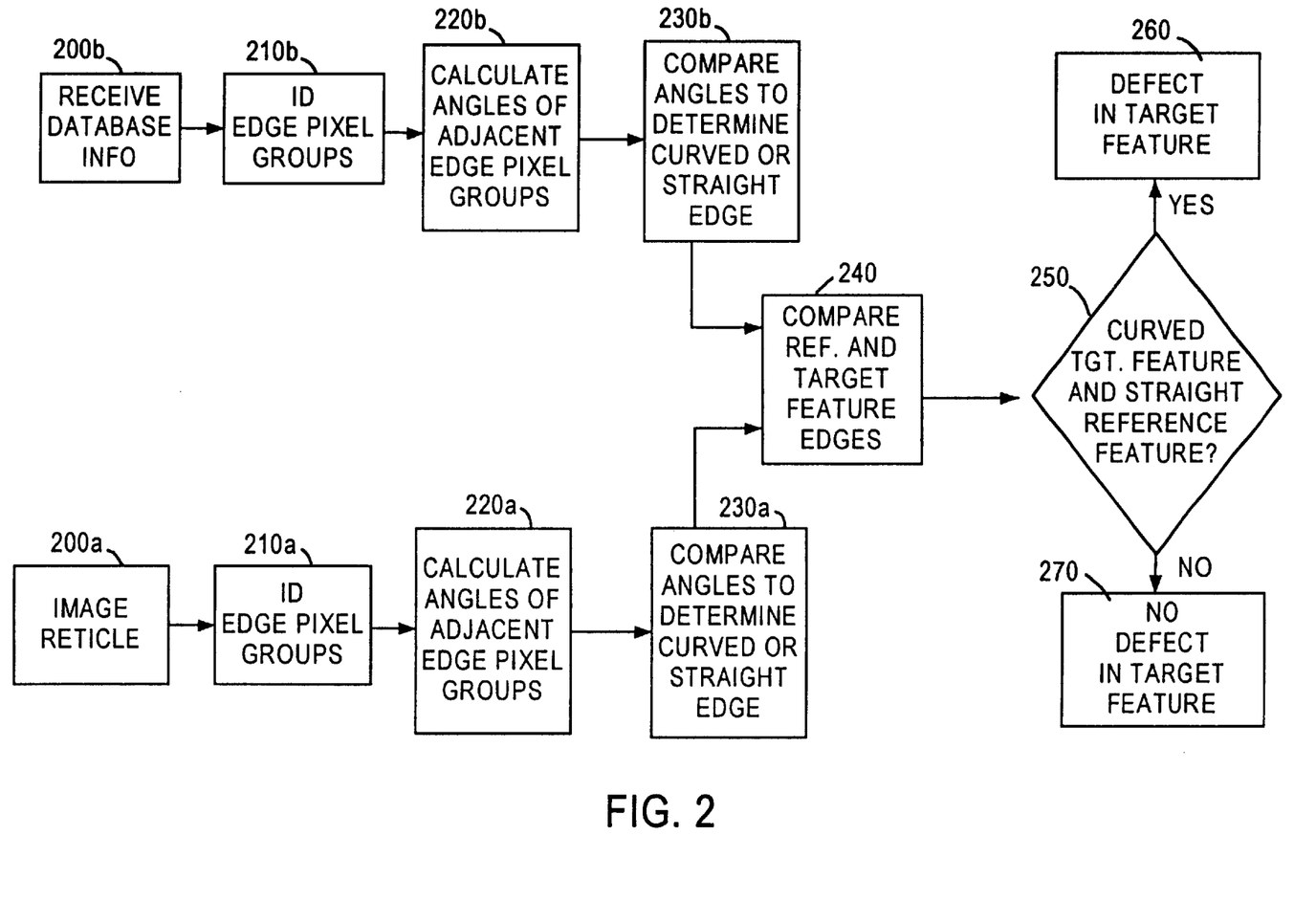
FIG. 2 is a flow chart illustrating sequential steps in a method according to an embodiment of the present invention.
Figure 3:
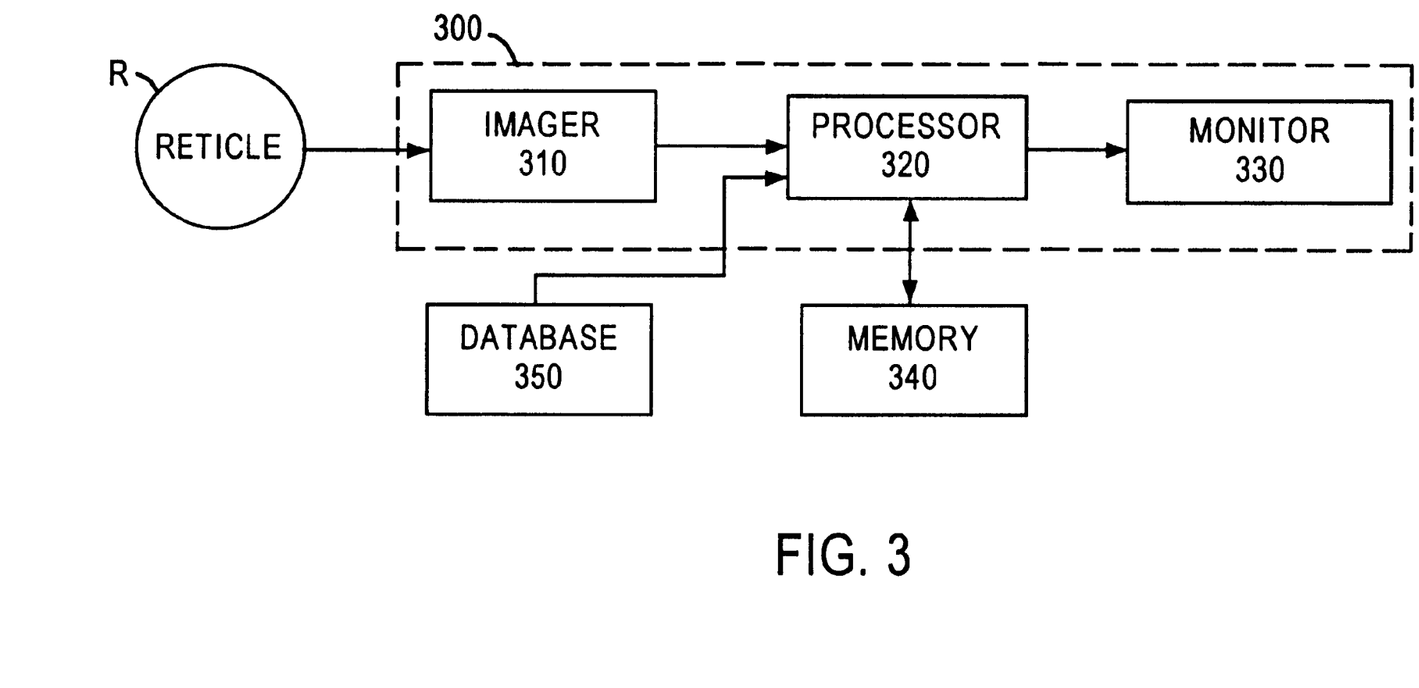
FIG. 3 is a block diagram that illustrates an embodiment of the invention.

An embodiment of the present invention is illustrated in FIGS. 2–9. The present invention is implemented at an inspection tool 300, as shown in FIG. 3, comprising an imager 310 for imaging the surface of a reticle R at high speed, typically using a photo multiplier tube (PMT) or CCD and an illumination source such as a lamp or a laser. Reticle R, typically comprising metal features on a transparent substrate (such as chrome on a glass surface), can be imaged by transmitting light through the substrate to the CCD, by reflecting light from the features to the CCD, or both. Inspection tool 300 further comprises a processor 320, which preferably performs the analysis disclosed herein electronically, and a monitor 330 for displaying results of the analyses of processor 320. Processor 320 can be in communication with a conventional reticle reference design database 350 and a memory device 340, such as a semiconductor memory. The functions of processor 320 are preferably implemented in hardware such as logic gates, for increased speed compared to software-implemented processing.

FIG. 2 is a general overview of the defect detection process of the present invention. The inventive process has two major channels that are almost identical: a reference (database) channel at the top of the diagram, and an inspected channel at the bottom of the diagram. At step 200*a* in FIG. 2, reticle R is imaged by imager 310 in a conventional manner and the image received by processor 320, which processes the image as a plurality of data elements called "pixels", each pixel having a gray level and associated with a location on reticle R.

The reference data of step 200*b* can be either from a database or from imager 310. If from the database, it can be obtained by using, for example, the system described in U.S. Pat. No. 5,907,628, which is incorporated herein by reference. On the other hand, the data can be obtained from a corresponding location on an adjacent die using well known techniques such as splitting the input of imager 310 into two channels, and providing a delay of one cell or die width in one channel.

Figure 4:
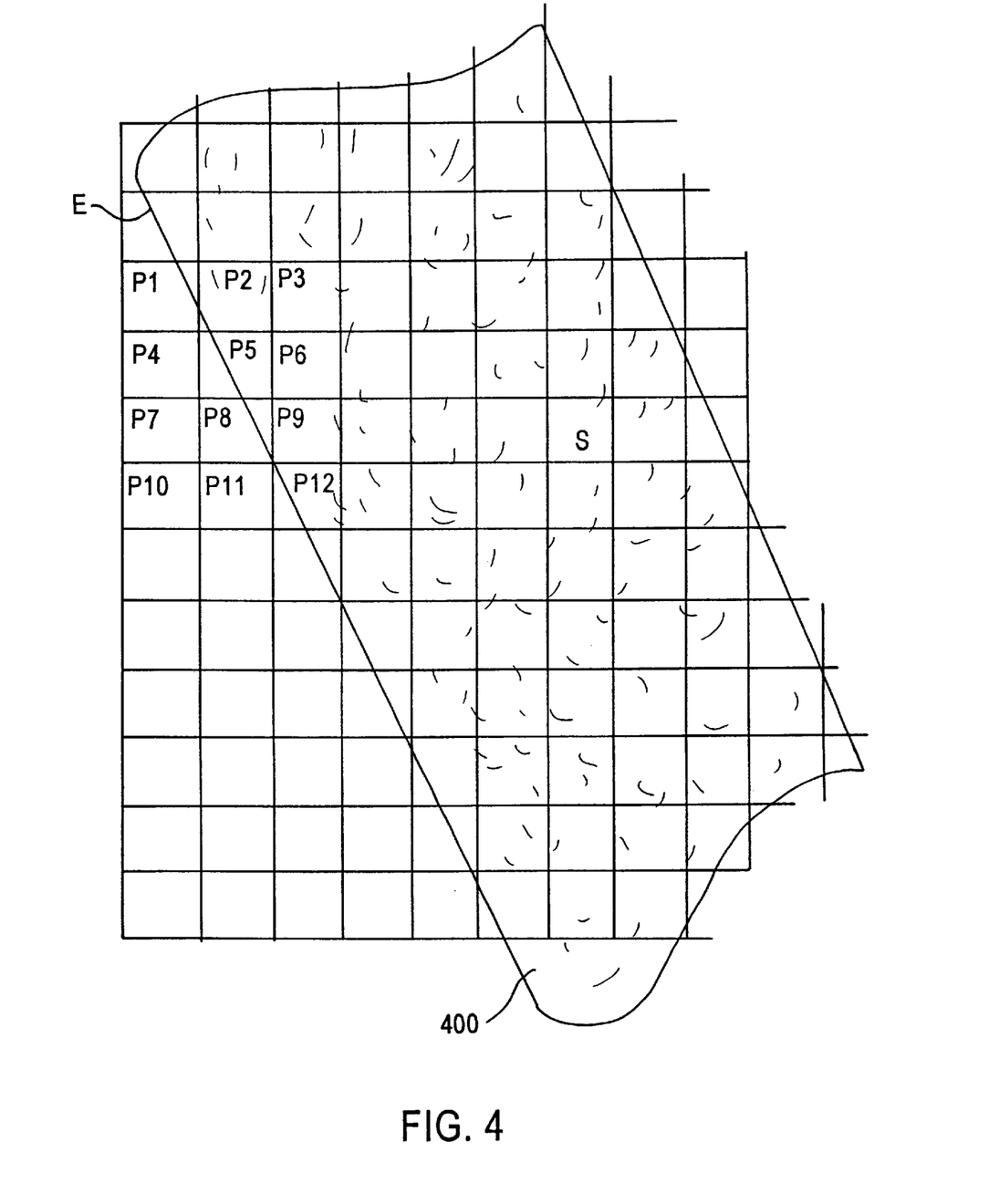
FIG. 4 illustrates the image-forming process used in practicing an embodiment of the present invention.

FIG. 4 represents an ideal reticle feature 400 on reticle R (e.g., as feature 400 would appear in database 350), having edge E and a surface S. The array of squares represents how pixels are formed, showing how much gray would be in each pixel; for example, pixels P1-P12 laying near edge E. An actual feature on reticle R corresponding to feature 400 would typically look similar to feature 400, with slight deviations. Actual pixels would typically be a matrix of numbers representing their gray levels, each pixel associated with x and y coordinates corresponding to its position in the image of feature 400.

At steps 210*a*, 210*b*, the pixels of the inspected channel are analyzed to identify groups of pixels associated with an edge of the feature of reticle R to be inspected by the present invention, and the reference channel pixels are analyzed to identify groups of pixels associated with an edge of a corresponding feature in the reference, as by comparing the gray levels of the pixels within each group. If any two pixels within a group, such as a 2×2 matrix of pixels, differ in gray level by a predetermined threshold amount, it indicates that the group straddles a feature edge.

At steps 220*a*, 220*b*, each of the identified edge pixel groups are mapped to angles (i.e., translated into angles from gray levels) by fitting a plane through all the pixels in the group based on the gray levels of the pixels of the group, as by using a least squares calculation, and calculating the angle between a reference line (e.g. the positive x-axis) and a line at the intersection of the fitted plane and a reference plane, such as the plane passing through the x and y coordinates of the pixels. At steps 230*a*, 230*b*, the angles of adjacent edge pixel groups (e.g., four adjacent groups) are compared to each other. If they are substantially the same, then the edge is determined to be straight in that local area; if they differ by more than a threshold amount, the edge is determined to be curved. If a curved edge exists in the image channel at step 230*a* and does not exist in the reference channel at step 230*b*, it is determined at step 240 that there is a defect in the inspected feature.

Steps 210*a* and 210*b*, wherein small groups of pixels are identified as laying on a feature edge, will now be described in greater detail with reference to FIG. 5 and the flow chart of FIG. 6A. In this step, the gray levels of four adjacent pixels, such as a 2×2 matrix of pixels, are compared. If the difference between the gray levels of any two of the four pixels is greater than a threshold value, the array is identified as laying on a feature edge.

Figure 5:
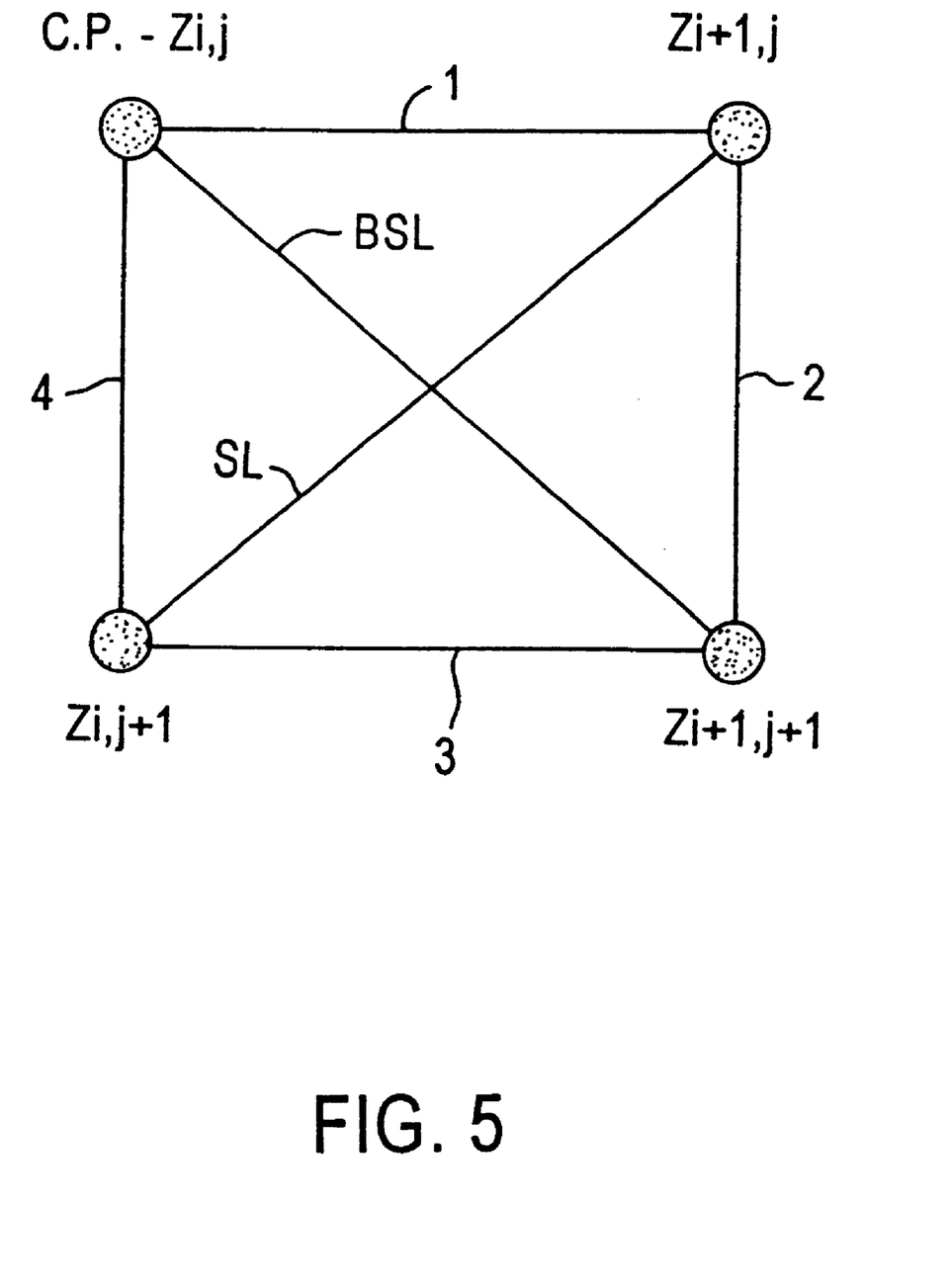
FIG. 5 illustrates a pixel span used in practicing a method according to an embodiment of the present invention.

FIG. 5 illustrates a 2×2 array of four pixels $Z_{ij}$, $Z_{i+1,j}$, $Z_{i,j+1}$, $Z_{i+1,j+1}$ to be compared. Z represents their gray level value, i and j represent their x- and y-axis coordinates, respectively, and C.P. denotes a "current pixel"; that is, an arbitrarily chosen pixel to which the result of the following procedure is related. The i-axis runs from left to right and the j-axis runs downward.

At step 601, current pixel C.P. is checked to ensure that its gray level is within a valid range by comparing its gray level against a high and low threshold value. If C.P.'s gray level does not fall within range, thereby indicating it does not lie near an edge, another pixel is chosen as the current pixel in step 602. If C.P.'s gray level is within range, then the absolute value of the differences in gray levels between C.P. and each of the other pixels in the array are calculated, and the differences between gray levels between each of the other pixels and each other are calculated (see step 603). In other words, gray levels of the following six pairs of pixels are compared:

C.P and Zi+1,j
C.P. and Zi,j+1
C.P. and Zi+1,j+1
Zi+1,j and Zi,j+1
Zi+1,j and Zi+1,j+1
Zi,j+1 and Zi+1,j+1

Next, the gray level differences or "gradients" are compared to an appropriate threshold value. At step 604, the differences between pairs of pixels orthogonally adjacent to each other (see sides 1–4) are compared to a contrast threshold value; e.g., a gray level value of about 40. At step 605, the differences between diagonally adjacent pixels (see SL and BSL lines) are compared to a diagonal threshold value. The orthogonally adjacent and diagonal pixel pairs are compared to different threshold values to account for the fact that the distance between diagonal pixels is longer than the distance between orthogonally adjacent pixels, and influences their gray level gradients.

If the gray level gradient of none of the six pairs of pixels is greater than or equal to the threshold value it was compared to in steps 604 and 605, at step 606 it is determined that the 2×2 array of pixels does not lay on a feature edge, and at step 607 another current pixel is chosen. However, if the gray level gradient of any of the six pixel pairs is greater than or equal to the threshold value they were compared to, the analysis of the array continues at step 608, where the array is checked to determined if it is forming a ridge or a "saddle" rather than laying on a feature edge. This test is performed by comparing the gray levels of the pairs of pixels of the diagonals SL, BSL of the array. If the lowest gray level of the slash diagonal (SL) is greater than the highest gray level of the backslash diagonal (BSL), or the lowest gray level of BSL is greater than the highest gray level of SL, then it is determined that the array forms a ridge or a saddle, and another current pixel is chosen at step 609. Otherwise, it is determined at step 610 that the array lies on a feature edge.

Referring again to FIG. 2, steps 220*a*, 220*b*, wherein the gray levels of pixel groups laying on the feature edge are converted to angles, will be explained in detail with reference to FIG. 5, the flow chart of FIG. 6B, and FIG. 7. Each of the four pixels $Z_{ij}$, $Z_{i+1,j}$, $Z_{i,j+1}$, $Z_{i+1,j+1}$ of the 2×2 array of FIG. 5 can be considered as a data point of a three dimensional graph 700, as shown in FIG. 7, wherein the x and y coordinates of the positions of the pixels in the image of the feature correspond to the x and y dimensions of graph 700, and the gray levels of the pixels correspond to its z dimension. The angle to be calculated is the angle α between the positive x-axis (or "reference line") and an intersection line IL of a plane P1 that fits the four data points with the x-y plane P2 (or "reference plane") through the x and y coordinates of the pixels.

The well-known least squares method is used to find the plane P1 which fits the four pixels. The equation of a plane in three dimensions (i,j,z) is:

$$Ai+Bj+z+C=0 \qquad (1)$$

The application of the least squares method to equation (1) yields the following equation:

$$\Sigma\Sigma[Z_{i,j}-(Ai+Bj+C)]^2=\epsilon^2 \qquad (2)$$

where ΣΣ is over i and j respectively, and $\epsilon^2$ is the error that is to be minimized by the least squares method.

Differentiation of equation (2) in respect to each of the variables A,B,C minimizes the sum of the errors:

$$\Sigma\Sigma Z_{i,j}i-\Sigma\Sigma Ai^2-\Sigma\Sigma Bji-\Sigma\Sigma Ci=0 \qquad (3)$$

$$\Sigma\Sigma Z_{i,j}j-\Sigma\Sigma Aij-\Sigma\Sigma Bj^2-\Sigma\Sigma Cj=0 \qquad (4)$$

$$\Sigma\Sigma Z_{i,j}-\Sigma\Sigma Ai-\Sigma\Sigma Bj-\Sigma\Sigma C=0 \qquad (5)$$

The i,j coordinates are defined as follows: the current pixel (C.P.) is the origin of axes i and j, namely (0,0); hence, i ranges from 0 to 1, as does j. Variable z is the gray level $Z_{ij}$. Applying these values in equations (3)–(5) results in:

$$2A+B+2C=Z_{10}+Z_{11} \qquad (6)$$

$$A+2B+2C=Z_{01}+Z_{11} \qquad (7)$$

$$2A+2B+4C=Z_{00}+Z_{01}+Z_{10}+Z_{11} \qquad (8)$$

Using equations (6)–(8), the variables A,B,C can be expressed as functions of $Z_{00}$, $Z_{01}$, $Z_{10}$, and $Z_{11}$.

Since the coordinates of the local plane P1 and the global axes x,y,z of the image are based on the same system (the only difference is that they are shifted), plane P1 can pass from one system—the local system—to the global system (i.e., the image system). Hence, intersection line IL between planes P1 and P2 can be expressed directly from plane equation (1) by inserting the value z=0 to yield the equation of the x-y plane P1, the result being:

$$Ax+By+C=0 \qquad (9)$$

The angle α can be found from the gradient of line IL with respect to the x-axis, which is equal to tan α, hence:

$$\tan(\alpha)=-(A/B) \qquad (10)$$

Since the expression of variables A and B as functions of gray level values $Z_{00}$, $Z_{01}$, $Z_{10}$, and $Z_{11}$, is known (see equations (6)–(8)), the following expression can be derived, using well known mathematical manipulations, to transform gray level values into the angle α:

$$\tan\alpha = \frac{(Z_{00}-Z_{11})+(Z_{01}-Z_{10})}{-(Z_{00}-Z_{11})+(Z_{01}-Z_{10})} \qquad (11)$$

Figure 6A:
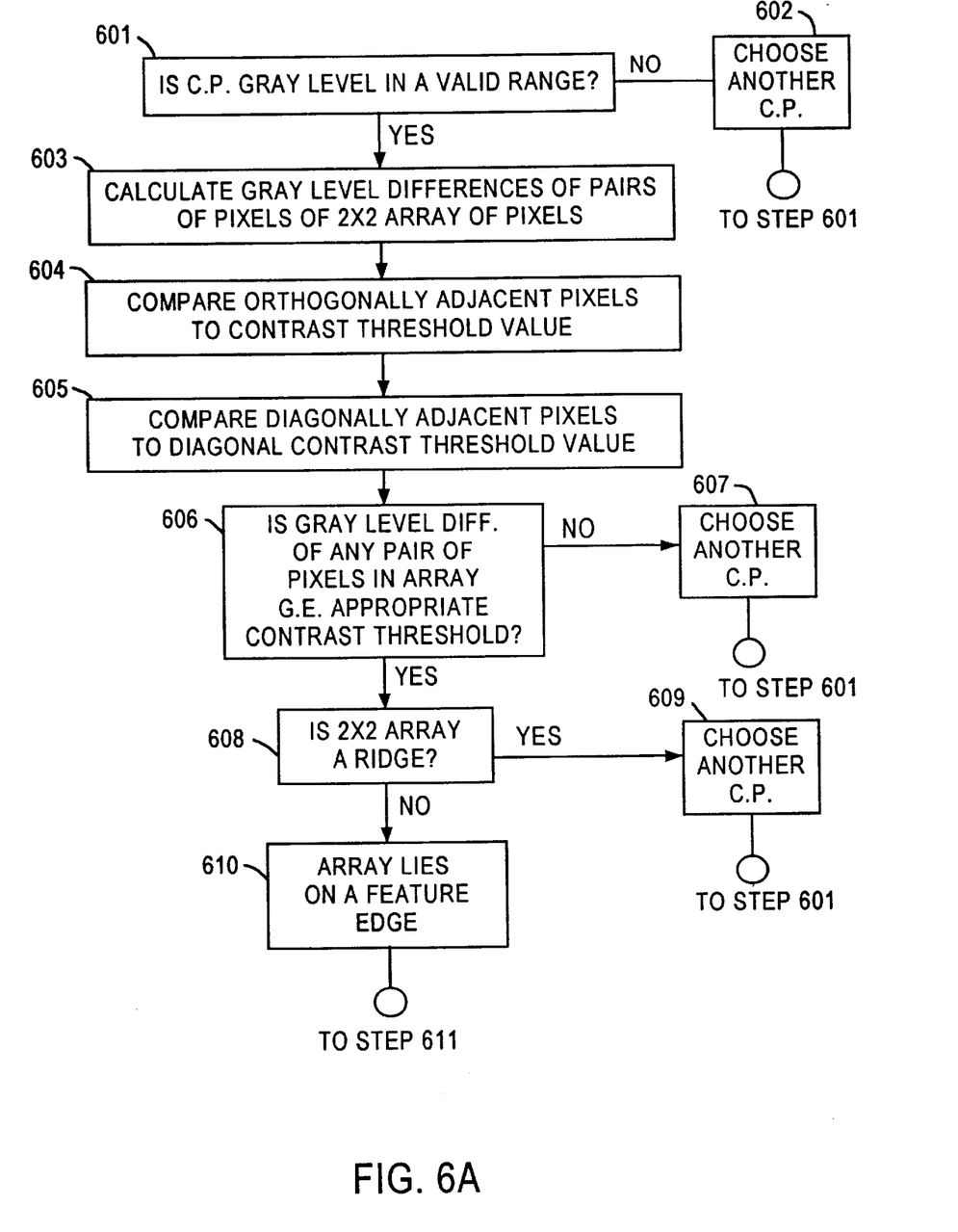
FIGS. 6A and 6B are flow charts illustrating sequential steps in a method according to an embodiment of the present invention.
Figure 6B:
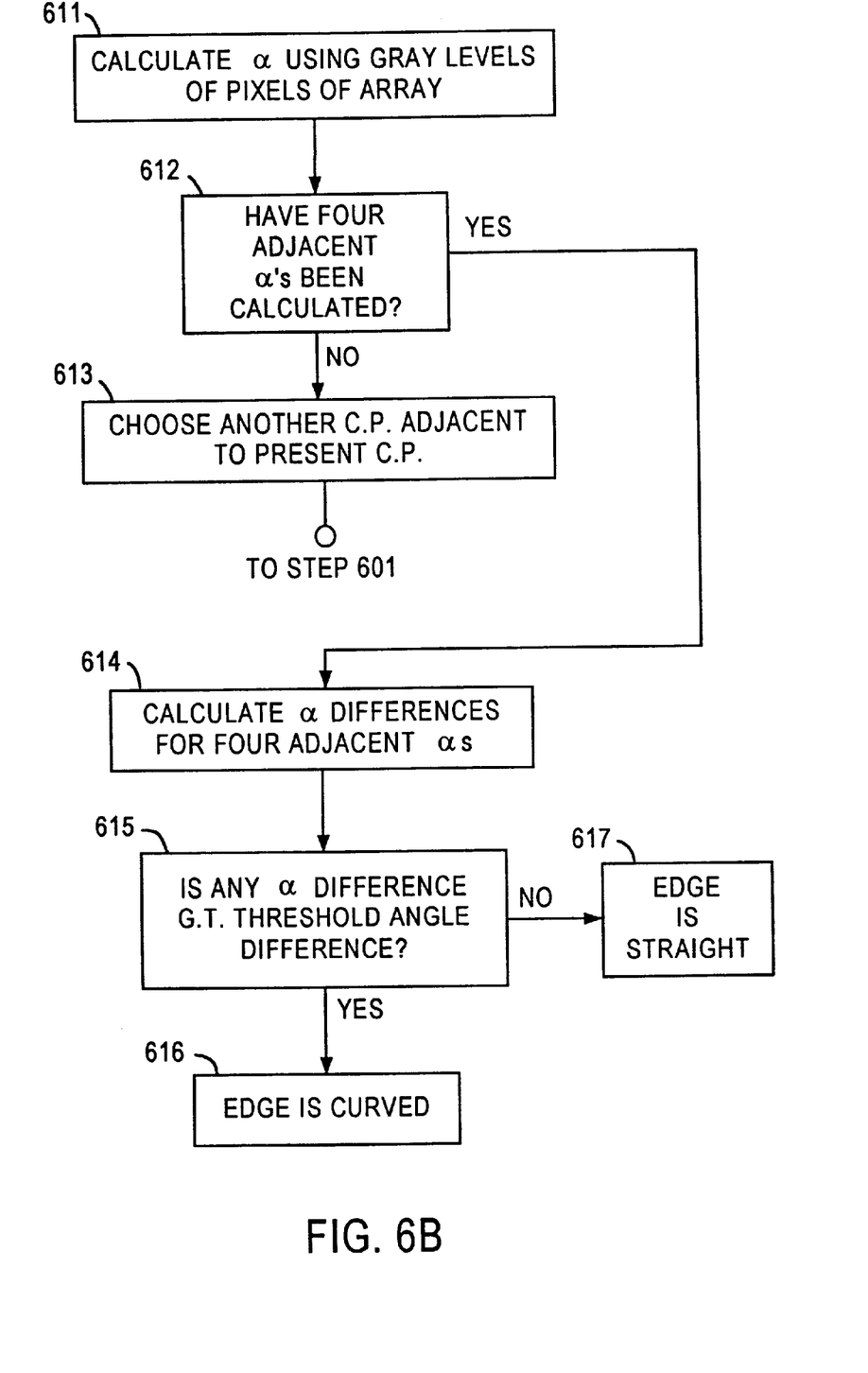
Figure 7:
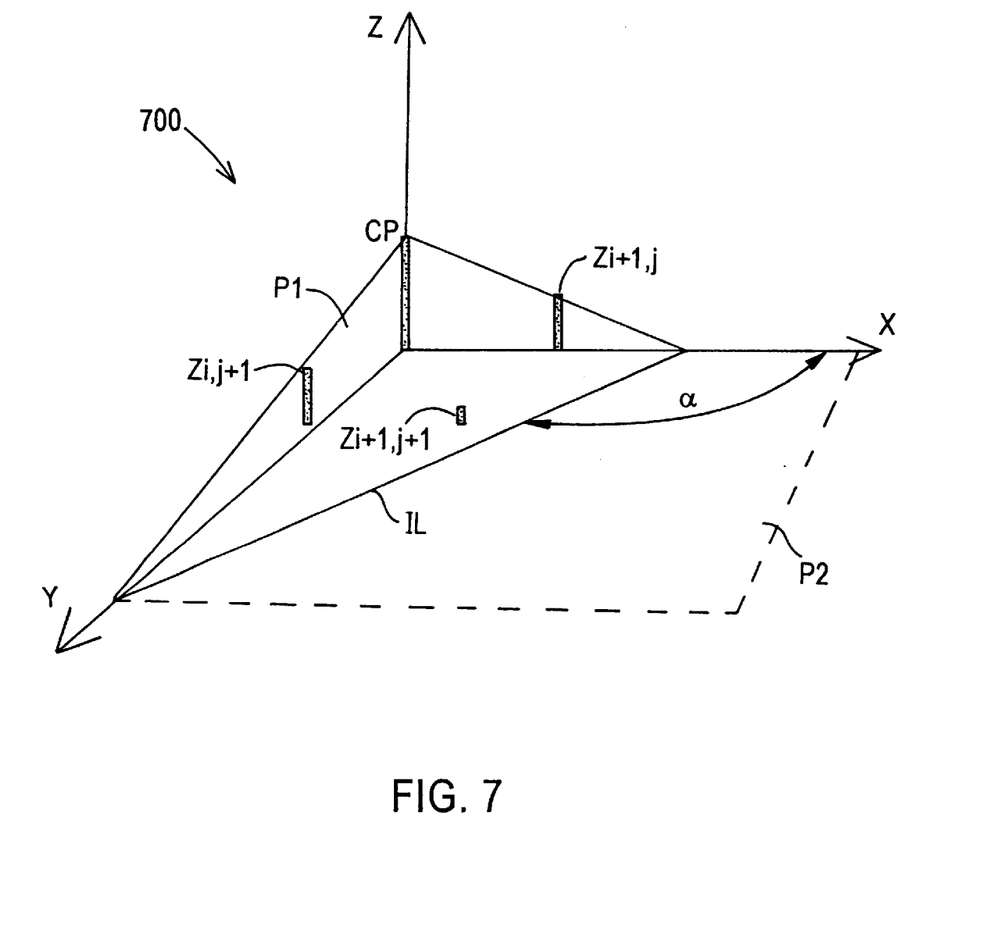
FIG. 7 illustrates an angle and a plane calculated in an embodiment of the present invention.
Figure 8:
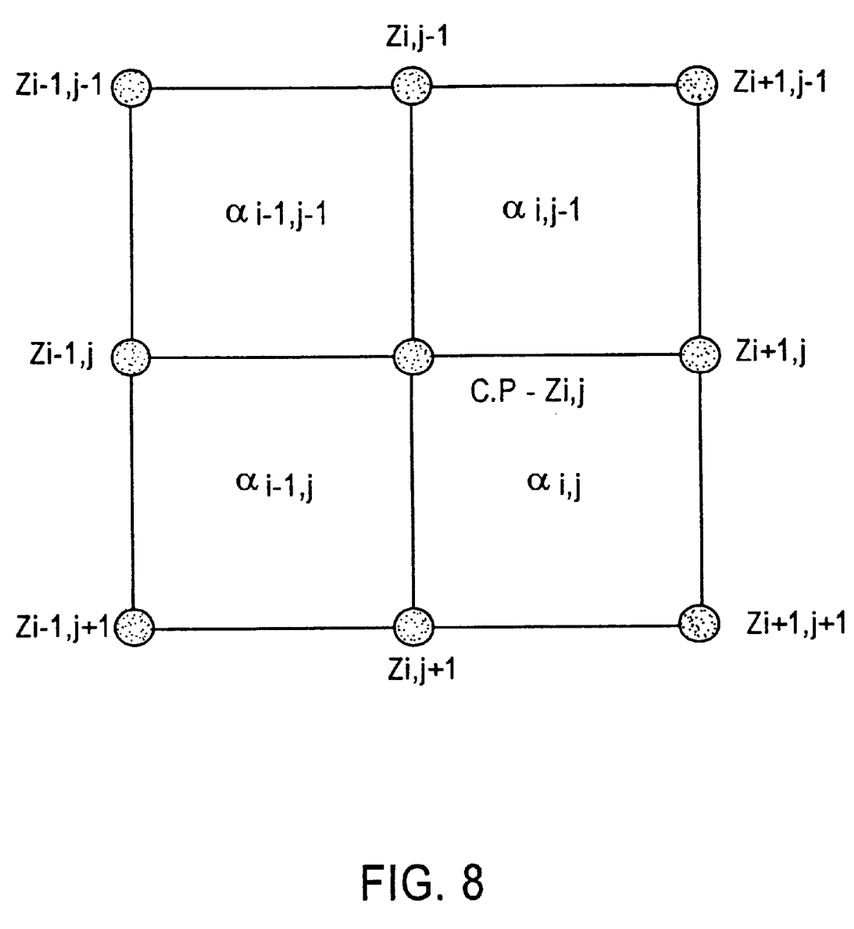
FIG. 8 illustrates an array of pixels used in practicing a method according to an embodiment of the present invention.

Referring now to FIG. 6B, at step 611, the angle a is calculated using equation (11) for the 2×2 array of pixels found to be laying on the feature edge in step 610 of FIG. 6A. Next, the above-described process of steps 601–611 is repeated using another pixel adjacent to C.P. as the current pixel until a number of adjacent angles α have been calculated (see steps 612, 613); e.g., until four adjacent 2×2 arrays of pixels are identified as laying on the feature edge and their angles α calculated. Preferably, for purposes of symmetry, the four adjacent arrays form a 3×3 matrix with C.P. in its center, as shown in FIG. 8. Referring again to FIG. 4, such a 3×3 array is comparable to an array of pixels P1–P9 with pixel P5 in the center, comprising four 2×2 arrays containing the following pixels:

P1, P2, P4, P5
P2, P3, P5, P6
P4, P5, P7, P8
P5, P6, P8, P9

Of course, one or more of the 2×2 pixel arrays analyzed may not yield eligible α values, such as if they do not lie on a feature edge. If so, that array is not used in the calculations that follow.

Referring again to FIG. 2, steps 230a, 230b, wherein the calculated angles α are compared with each other to determine whether the feature edge is curved or straight, will be explained in detail with reference to FIG. 8 and the flow chart of FIG. 6B. After a predetermined number of angles α; for example, an n x n array of adjacent angles α, such as αij, αi,j-1, αi-1,j-1 and αi-1,j of FIG. 8 have been calculated, they are compared to each other, and if they are substantially equal to each other, the feature edge is determined to be straight. On the other hand, if the angles α are not substantially equal to each other, the feature edge is determined to be curved.

For example, at step 614, the differences between each of the four angles α and each other are calculated (a total of six angle differences), and at step 615 the a differences are compared to a threshold angle difference. If any of the a differences are greater than the threshold angle difference, the feature edge is determined to be curved at step 616. If none of the α differences are greater than the threshold angle difference, the feature edge is determined to be straight at step 617. Different threshold angle differences can be used to improve sensitivity; for example, it is preferred that the smaller the gray level differences between the pixels of each 2×2 array used to determine the angles, the wider the angle differences allowed to define a curved edge.

As discussed above, adverting to FIG. 2, the steps 601–617 are performed on two streams of pixel data: on pixels of the inspected channel (steps 200a–230a) and on corresponding pixels of the reference channel (steps 200b–230b) to determine if the edge of the target (inspected) feature is straight or curved, and to determine if the corresponding reference feature edge is straight or curved. At step 240, the reference and target feature edges are compared, and it is determined at steps 250–270 that a defect exists in the target feature if the target feature edge is curved and the corresponding reference feature edge is straight. In one embodiment of the present invention, "flags" are set whenever the reference channel or the inspected channel finds a curved edge. If a flag is set in the inspected channel and a flag or flags is not set at approximately the same location in the reference channel, then the target feature is determined to be defective. Using this flag-comparison technique, perfect registration is not required between the inspected and reference channels, thereby reducing inspection time.

Figure 9:
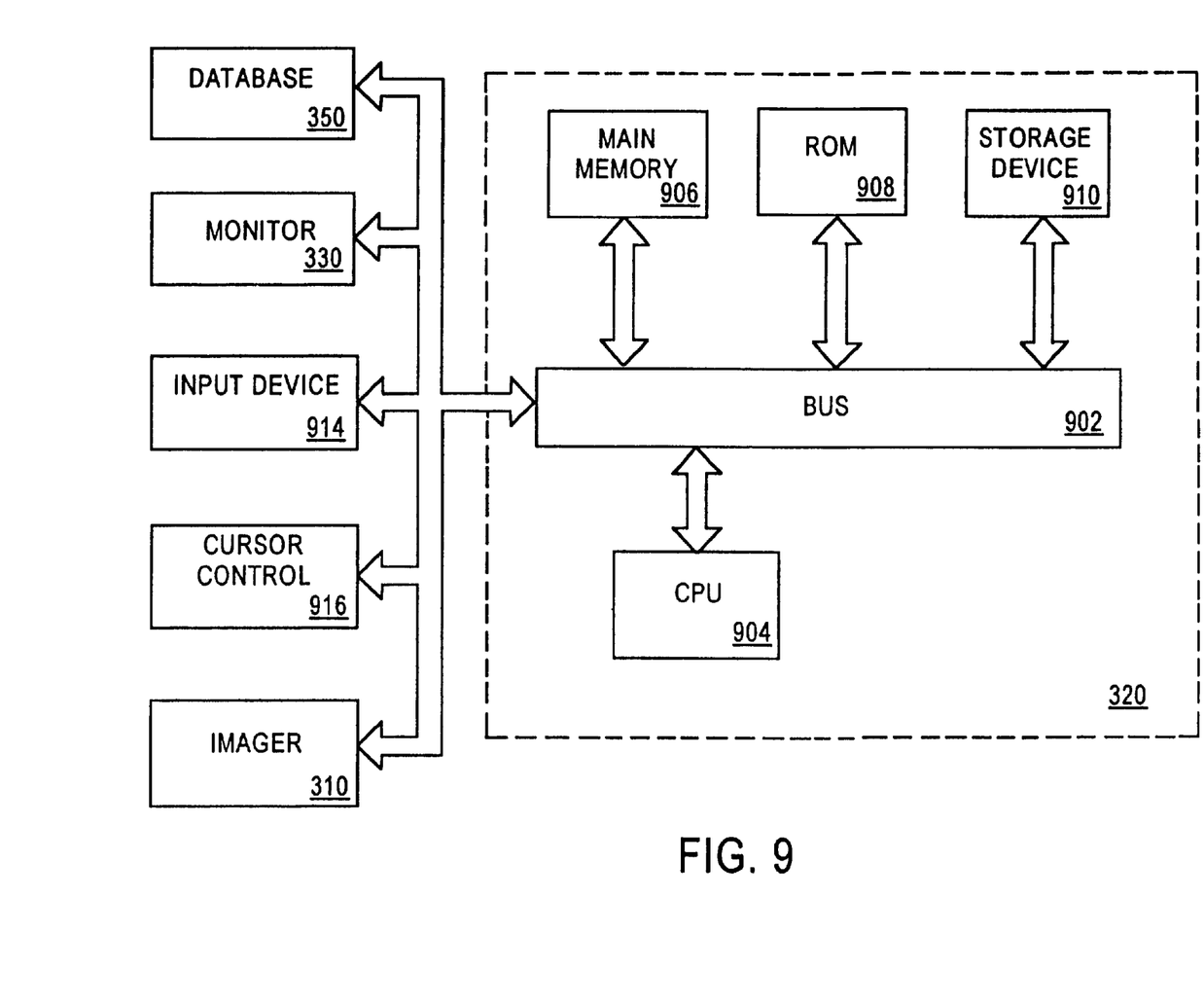
FIG. 9 is a block diagram that illustrates an embodiment of the invention.

FIG. 9 is a block diagram that illustrates an embodiment of the invention shown in FIG. 3. According to this embodiment, processor 320, as shown in FIG. 3, includes a bus 902 or other communication mechanism for communicating information, and a central processing unit (CPU) 904 coupled with bus 902 for processing information. Processor 320 also includes a main memory 906, such as a random access memory (RAM) or other dynamic storage device, coupled to bus 902 for storing information and instructions to be executed by CPU 904. Main memory 906 also may be used for storing temporary variables or other intermediate information during execution of instructions to be executed by CPU 904. Processor 320 further includes a read only memory (ROM) 908 or other static storage device coupled to bus 902 for storing static information and instructions for CPU 904. A storage device 910, such as a magnetic disk or optical disk, is coupled to bus 902 for storing information and instructions. Storage device 910 may also serve as memory 340 in FIG. 3.

Processor 320 is coupled, as via bus 902, to monitor 330 (FIG. 3), such as a cathode ray tube (CRT), for displaying information to the user. An input device 914, including alphanumeric and other keys, is coupled to bus 902 for communicating information and command selections to CPU 904. Another type of user input device is cursor control 916, such as a mouse, a trackball, or cursor direction keys for communicating direction information and command selections to CPU 904 and for controlling cursor movement on monitor 330.

Imager 310 (FIG. 3) inputs data representative of images of a reticle under inspection, as discussed above, to bus 902. Such data may be stored in main memory 906 and/or storage device 340, and used by CPU 904 as it executes instructions. Imager 310 may also receive instructions via bus 902 from CPU 904.

Likewise, database 350 (FIG. 3) inputs data representative of a substantially defectless reticle, as discussed above, to bus 902. Such data may be stored in main memory 906 and/or storage device 340, and used by CPU 904 as it executes instructions.

The invention is related to the use of processor 320 for inspecting the surface of a reticle. According to an embodiment of the invention, inspection of the reticle is provided by processor 320 in response to CPU 904 executing one or more sequences of one or more instructions contained in main memory 906. Such instructions may be read into main memory 906 from another computer-readable medium, such as storage device 910. Execution of the sequences of instructions contained in main memory 906 causes CPU 904 to perform the process steps described above. One or more processors in a multi-processing arrangement may also be employed to execute the sequences of instructions contained in main memory 906. As discussed above, in alternative embodiments, hard-wired circuitry may be used in place of or in combination with software instructions to implement the invention. Thus, embodiments of the invention are not limited to any specific combination of hardware circuitry and software. The programming of the apparatus is readily accomplished by one of ordinary skill in the art provided with the flow charts of FIGS. 2, 6A and 6B.

The term "computer-readable medium" as used herein refers to any medium that participates in providing instructions to CPU 904 for execution. Such a medium may take many forms, including but not limited to, non-volatile media, volatile media, and transmission media. Non-volatile media include, for example, optical or magnetic disks, such as storage device 910. Volatile media include dynamic memory, such as main memory 906. Transmission media include coaxial cable, copper wire and fiber optics, including the wires that comprise bus 902. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with features of holes, a RAM, a PROM, and EPROM, a FLASH-EPROM, any other memory chip or cartridge, or any other medium from which a computer can read.

Various forms of computer-readable media may be involved in carrying out one or more sequences of one or more instructions to CPU 904 for execution. For example, the instructions may initially be borne on a magnetic disk of a remote computer. The remote computer can load the instructions into its dynamic memory and send the instructions over a telephone line using a modem. A modem local to processor 320 can receive the data on the telephone line and use an infrared transmitter to convert the data to an infrared signal. An infrared detector coupled to bus 902 can receive the data carried in the infrared signal and place the data on bus 902. Bus 902 carries the data to main memory 906, from which CPU 904 retrieves and executes the instructions. The instructions received by main memory 906 may optionally be stored on storage device 910 either before or after execution by CPU 904.

Thus, the methodology of the present invention enables accurate and reliable inspection of the straightness of feature edges by analyzing the gray level information of small groups of pixels to detect a feature edge and identify groups of pixels straddling an edge, and then mapping the gray level information of the edge pixel groups to angular values, which are compared to each other. This avoids the pixel-by-pixel comparison inspection of conventional reticle inspection tools, which can miss small local edge curvature or give inaccurate results. Furthermore, by calculating comparable angular values and edge straightness for a reference feature at substantially the same location on the reticle as the inspected feature, straight-line defects in the inspected feature edge can easily be determined. Still further, by flagging curved edges in the target feature and reference feature and comparing the location of flags in the target and reference features, defects can be detected without the need for perfect registration between the reference channel and the inspected channel, thereby reducing inspection time.

The present invention is applicable to the inspection of any photolithographic reticle used in the manufacture of semiconductor devices, and is especially useful for in-process inspection of reticles used in the manufacture of high density semiconductor devices with submicron design features.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein. For example, it should be appreciated that the inventive system and method can be implemented in a semiconductor wafer inspection system. A suitable system is disclosed in, for example, U.S. Pat No. 5,699,447, which is incorporated herein by reference. Of course, in this case the image is of a reflected light, rather than of transmitted light.

What is claimed is:

1. An inspection tool for inspecting a target feature formed on a surface, the inspection tool comprising:
   an imager to image the target feature to produce a matrix of pixels representative of the target feature, each pixel having a gray level and associated with an x and a y coordinate corresponding to its respective location on the surface; and
   a processor for:
   identifying a current pixel and a first plurality of pixels adjacent to the current pixel and each other associated with the feature edge;
   determining a first plane based on the x coordinate, the y coordinate and the gray level of each of the current pixel and the first plurality of pixels;
   calculating a first angle between a first reference line and a first intersection line at the intersection of the first plane and a reference plane;
   identifying a second current pixel and a second plurality of pixels adjacent to the second current pixel and each other associated with the feature edge;
   determining a second plane based on the x coordinate, the y coordinate and the gray level of each of the second current pixel and the second plurality of pixels;
   calculating a second angle between a second reference line corresponding to the first reference line, and a second intersection line at the intersection of the second plane and the reference plane; and
   comparing the first and second angles to determine whether a defect exists in the target feature.

2. The inspection tool of claim 1, wherein the processor is further configured to:
   identify the current pixel and first plurality of pixels associated with the feature edge by comparing the gray level of the current pixel and each of the first plurality of pixels with each other; and
   identify the second current pixel and second plurality of pixels associated with the feature edge by comparing the gray level of the second current pixel and each of the second plurality of pixels with each other.

3. The inspection tool of claim 2, wherein the processor is further configured to:
   calculate the differences in gray levels between the current pixel and each of the first plurality of pixels, and each of the first plurality of pixels and each other;
   compare the gray level differences to a contrast threshold value;
   determine that the current pixel and first plurality of pixels are associated with the feature edge when one of the gray level differences is greater than or equal to the contrast threshold value;
   calculate updated differences in gray levels between the second current pixel and each of the second plurality of pixels, and each of the second plurality of pixels and each other;
   compare the updated gray level differences to the contrast threshold value; and
   determine that the second current pixel and second plurality of pixels are associated with the feature edge when one of the updated gray level differences is greater than or equal to the contrast threshold value.

4. The inspection tool of claim 3, wherein the processor is further configured to:
   compare the gray level and updated gray level differences of pairs of pixels diagonally across from each other in 2×2 arrays with a diagonal contrast threshold value;
   determine that the current pixel and first plurality of pixels are associated with the feature edge when one of the diagonal gray level differences is greater than or equal to the diagonal contrast threshold value; and
   determine that the second current pixel and second plurality of pixels are associated with the feature edge when one of the updated diagonal gray level differences is greater than or equal to the diagonal contrast threshold value.

5. The inspection tool of claim 1, wherein the processor is further configured to determine the first plane based on a least squares analysis.

6. The inspection tool of claim 5, wherein the current pixel and first plurality of pixels are a first 2×2 array of pixels, and the second current pixel and second plurality of pixels are a second 2×2 array of pixels, wherein the processor is further configured to calculate the first and second angles, respectively, based on the following relationship:

$$\tan\alpha = \frac{(Z_{00} - Z_{11}) + (Z_{01} - Z_{10})}{-(Z_{00} - Z_{11}) + (Z_{01} - Z_{10})}$$

wherein $\alpha$ is the first angle and the second angle, respectively, the first and second digits of the subscripts correspond to the x and y coordinates, respectively, of each of the pixels of the arrays, and Z corresponds to the gray levels of each of the respective pixels of the arrays.

7. The inspection tool of claim 1, wherein the processor is further configured to determine the reference plane through only the x and y coordinates of the pixels.

8. The inspection tool of claim 1, wherein the processor is further configured to:
   identify a third current pixel and a third plurality of pixels adjacent to the third current pixel and each other associated with the feature edge;
   determine a third plane based on the x coordinate, the y coordinate and the gray level of each of the third current pixel and the third plurality of pixels;
   calculate a third angle between a third reference line corresponding to the first reference line, and a third intersection line at the intersection of the third plane and a reference plane;
   identify a fourth current pixel and a fourth plurality of pixels adjacent to the fourth current pixel and each other associated with the feature edge;
   determine a fourth plane based on the x coordinate, the y coordinate and the gray level of each of the fourth current pixel and the fourth plurality of pixels;
   calculate a fourth angle between a fourth reference line corresponding to the first reference line, and a fourth intersection line at the intersection of the fourth plane and the reference plane;
   wherein the current pixel and first plurality of pixels are a first 2×2 array of pixels, the second current pixel and second plurality of pixels are a second 2×2 array of pixels, the third current pixel and third plurality of pixels are a third 2×2 array of pixels, and the fourth current pixel and fourth plurality of pixels are a fourth 2×2 array of pixels;

wherein the first, second, third and fourth arrays are adjacent to each other on the matrix to form a 3×3 array of pixels with the current pixel in the center; and wherein the processor is further configured to compare the first, second, third and fourth angles to determine whether a defect exists in the target feature.

9. The inspection tool of claim 1, wherein the processor is further configured to:

determine that the edge is curved when the first and second angles are not substantially equal, and that the edge is straight when the first and second angles are substantially equal; and compare the target feature edge to an edge of a reference feature corresponding to the target feature to determine whether a defect exists in the target feature.

10. The inspection tool of claim 9, wherein the processor is further configured to:

receive a matrix of pixels representative of the reference feature, each reference feature pixel having a gray level and associated with an x and a y coordinate corresponding to substantially the same location on the surface as the target feature pixels;

identify a current reference feature pixel and a first plurality of reference feature pixels adjacent to the current reference pixel and each other associated with the reference feature edge;

determine a first reference feature plane based on the x coordinate, the y coordinate and the gray level of each of the current reference feature pixel and the first plurality of reference feature pixels;

calculate a first reference feature angle between a first base reference line and a first intersection line at the intersection of the first reference feature plane and a base reference feature plane;

identify a second current reference feature pixel and a second plurality of reference feature pixels adjacent to the second current reference feature pixel and each other associated with the reference feature edge;

determine a second reference feature plane based on the x coordinate, the y coordinate and the gray level of each of the second current reference feature pixel and the second plurality of reference feature pixels;

calculate a second reference feature angle between a second base reference line corresponding to the first base reference line, and a second intersection line at the intersection of the second reference feature plane and the base reference feature plane;

determine that the reference feature edge is curved when the first and second reference feature angles are not substantially equal, and that the reference feature edge is straight when the first and second reference feature angles are substantially equal; and determine that a defect exists in the target feature when the target feature edge is curved and the reference feature edge is straight.

* * * * *